United States Patent
Petersen et al.

(10) Patent No.: US 10,228,338 B2
(45) Date of Patent: Mar. 12, 2019

(54) GAS SENSOR

(71) Applicant: Robert Bosch GmbH, Stuttgart (DE)

(72) Inventors: Andreas Petersen, Marbach (DE);
Andreas Krauss, Teubingen (DE);
Michael Badeja, Reutlingen (DE)

(73) Assignee: Robert Bosch GmbH, Stuttgart (DE)

(*) Notice: Subject to any disclaimer, the term of this patent is extended or adjusted under 35 U.S.C. 154(b) by 212 days.

(21) Appl. No.: 15/429,443

(22) Filed: Feb. 10, 2017

(65) Prior Publication Data
US 2017/0227484 A1    Aug. 10, 2017

(30) Foreign Application Priority Data
Feb. 10, 2016 (DE) .......... 10 2016 201 950

(51) Int. Cl.

| | |
|---|---|
| *B01L 5/00* | (2006.01) |
| *G01N 1/22* | (2006.01) |
| *G01N 33/00* | (2006.01) |
| *G01N 27/12* | (2006.01) |
| G01N 21/3504 | (2014.01) |
| G01N 15/00 | (2006.01) |

(52) U.S. Cl.
CPC .............. *G01N 27/125* (2013.01); *B01L 5/00* (2013.01); *G01N 1/22* (2013.01); *G01N 33/0039* (2013.01); *G01N 21/3504* (2013.01); *G01N 33/0004* (2013.01); *G01N 2001/2244* (2013.01); *G01N 2015/0026* (2013.01); *Y02A 50/247* (2018.01)

(58) Field of Classification Search
CPC .... G01N 27/125; G01N 33/0039; G01N 1/22; G01N 2001/2244; G01N 2015/0026; G01N 21/3504; G01N 33/0004; Y02A 50/247; B01L 5/00
See application file for complete search history.

(56) References Cited

U.S. PATENT DOCUMENTS

| | | | |
|---|---|---|---|
| 2005/0007119 A1* | 1/2005 | Belyakov | G01N 1/22 324/464 |
| 2005/0045477 A1* | 3/2005 | Wei | B82Y 30/00 204/431 |
| 2010/0071460 A1* | 3/2010 | Fleischer | G01N 27/4143 73/335.05 |

FOREIGN PATENT DOCUMENTS

| | | |
|---|---|---|
| DE | 10 2008 048 715 A1 | 4/2010 |
| EP | 1 104 884 A2 | 6/2001 |

* cited by examiner

*Primary Examiner* — Jennifer Wecker
(74) *Attorney, Agent, or Firm* — Maginot, Moore & Beck LLP

(57) ABSTRACT

A measuring device for determining a gas concentration includes a gas-sensitive element, a sensing device, a stimulation unit, and a processing unit. The gas-sensitive element is configured to absorb a gas. The sensing device is configured to determine a parameter of the gas-sensitive element in a predetermined time period, where the parameter depends on an absorbed quantity of the gas. The stimulation unit is configured to stimulate the gas-sensitive element and accelerate desorption of the gas out of the gas-sensitive element. The processing unit is configured to determine a rate of change of the parameter, to control the stimulation such that a concentration of the gas in the gas-sensitive element lies outside of an equilibrium state, and to determine the gas concentration based on the rate of change.

10 Claims, 4 Drawing Sheets

GAS SENSOR

This application claims priority under 35 U.S.C. § 119 to patent application no. DE 2016 201 950.3, filed on Feb. 10, 2016 in Germany, the disclosure of which is incorporated herein by reference in its entirety.

The disclosure relates to a gas sensor. In particular, the disclosure relates to a device and a method for the improved determination of the concentration of a gas.

BACKGROUND

A gas sensor is set up to determine the concentration of a predetermined gas, for example ozone, in a fluid medium such as air. For this purpose, the gas sensor follows the indirect measuring principle, in which a gas-sensitive element is provided, on which it is possible to determine a parameter that can be influenced by the gas concentration. Ideally, the parameter depends only on the concentration of the gas to be measured (selectivity). Even small changes in the gas concentration are intended to measurably influence the parameter (sensitivity). There should be a defined relationship between the gas concentration and the measurable parameter (accuracy). The property to be measured should change as quickly as possible with the gas concentration (short measuring time). In addition, these changes should be reversible (service life of the sensor). The concentration should be measurable with little outlay (costs and ability to be miniaturized) and the measurement method should need only little energy, in order to be suitable for mobile application, for example in a Smartphone.

A small and indirectly measuring gas sensor is usually based on a field effect transistor (FET) or a metal oxide layer (MOX layer). In the FET-based sensors, the gas to be measured normally influences the work function of a gas-sensitive layer applied to the gate electrode and therefore normally causes a change in the source-drain current. Examples of such sensors are described in the applications DE 10 2008 048 715 or EP 1 104 884 82.

In the gas sensors which are based on an MOX layer, the electrical resistance of a heatable MOX layer is measured. This resistance changes as a result of the presence of specific gases and their chemical interaction with the MOX layer (oxidation and reduction processes). In order to control the sensitivity and selectivity of the sensor for a predetermined gas, the MOX layer can be heatable. By means of thermal stimulation, the sensor can be kept in a defined state in order to ensure the desired measuring accuracy. The thermal stimulation is also called regeneration. Other types of regeneration are likewise possible, for example optical.

SUMMARY

The disclosure is based on the object of specifying an improved indirectly measuring gas sensor. The disclosure achieves this object by means of the subjects of the claims, detailed description, and drawings.

A method for determining a gas concentration comprises steps of absorbing the gas by means of a gas-sensitive element; determining a rate of change of a parameter of the element over a predetermined time period, wherein the parameter depends on the quantity of absorbed gas; stimulating the element in order to accelerate desorption of the gas out of the element, wherein the stimulation is carried out in such a way that the concentration of the gas in the element lies outside an equilibrium state; and determining the gas concentration on the basis of the rate of change.

It has been recognized that it is not necessary to wait until the sensor is in an equilibrium state with the gas in order to determine the gas concentration. Times in the range of up to several minutes usually elapse until the equilibrium state is assumed. In order to permit a faster measurement, it may be sufficient to determine the rate of change of the parameter of the element. In this case, the sensor is deliberately kept in a state outside the equilibrium. For this purpose, the sensor can be stimulated alternatively as a function of the rate of change or in a time-controlled manner, in particular periodically. As a result, the concentration of the gas can be determined quickly and economically and the power consumption of the method can be reduced. The predetermined time period in which the rate of change is determined is preferably as immediately as possible after the beginning or ending of the stimulation of the element. At these times, the rate of change is advantageously high, so that the measurement error can be relatively small. In addition, the size of the time window can be chosen to be smaller as a result, so that the determination can demand less time.

Preferably, the stimulation is carried out periodically, in order to keep the concentration of the gas in the element in a predetermined range. In other words, it is preferred to keep the element within a predetermined range of the non-equilibrium state by means of alternating stimulation and removal of the stimulus. For example, it can be attempted to keep the element in a range in which the parameter is about 50 to 80% of the value in the equilibrium state. As a result, the rate of change can also be determined repeatedly successively in a targeted manner.

It is particularly preferred for the determination of the gas concentration to be based on the rate of change immediately after the stimulus has been switched off. It has been shown that the parameter is particularly stable directly after the stimulus has been switched off and permits low-noise determination of the parameter. This can be attributed partly to the fact that the measured values when the stimulus is switched off do not depend on the stimulation and therefore not on possible fluctuations or possible noise. The gas concentration can be determined in an improved manner on the basis of the rate of change.

It is particularly preferred for the gas concentration K to be determined on the basis of the relationship $$K = A \cdot \left(\frac{dR}{dt}\right)^B,$$

where R is the parameter and B is approximately 2. In other words, the gas concentration depends on the rate of change via the power law, wherein the power of the rate of change virtually always approximately assumes a value of 2. Then, in the formula indicated above, only A exists as a free parameter. This one free parameter can permit simple and economical calibration of the method with only one measured value. Such a calibration is particularly suitable for products in the entertainment electronics sector, since the calibration can be carried out automatically as soon as a current gas concentration in the area of the gas-sensitive element is known. Regular calibrations make it possible to counteract possible sensor drift effectively. In further embodiments, more complex models for adjustment and calibration can also be used.

It is particularly preferred for the parameter to be determined electrically. In particular, the parameter can relate to the crossover behavior of a transistor or the electrical resistance of the element. In other embodiments, the parameter can also be read optically, for example. Here, physical contact with the gas-sensitive element is not required for the measurement.

The stimulation can likewise be carried out in different ways. In a first embodiment, the gas-sensitive element is heated for stimulation, in a second embodiment is irradiated by means of light of a predetermined wavelength and, in a third embodiment, is exposed to an electric field. Other stimuli which in each case have the object of removing absorbed gas from the gas-sensitive element are likewise possible.

A measuring device for determining a gas concentration comprises a gas-sensitive element for absorption of the gas; a sensing device for determining a parameter of the element, wherein the parameter depends on the absorbed quantity of the gas; a stimulation unit for stimulating the element, in order to accelerate desorption of the gas out of the element; and a processing unit. Here, the processing unit is set up to determine a rate of change of the parameter in a predetermined time period, to control the stimulation in such a way that the concentration of the gas in the element lies outside an equilibrium state, and to determine the gas concentration on the basis of the rate of change.

The measuring device can be constructed to be small and compact and, for example, find application in a mobile device such as a Smartphone. Response and reaction time of the measuring device can be shortened substantially as compared with a known measuring device. Power consumption of the measuring device can be reduced.

It is particularly preferred for the gas-sensitive element to comprise a metal oxide.

BRIEF DESCRIPTION OF THE DRAWINGS

The disclosure will now be described in more detail with reference to the appended figures, in which.

DETAILED DESCRIPTION

Although the technique according to the disclosure can be implemented in different ways, in the following text, purely by way of example, the basis will be the determination of a concentration of ozone by means of a metal oxide. Other gases can likewise be detected and, instead of the metal oxide, another element can also be used, in particular a field effect transistor.

Figure 1:
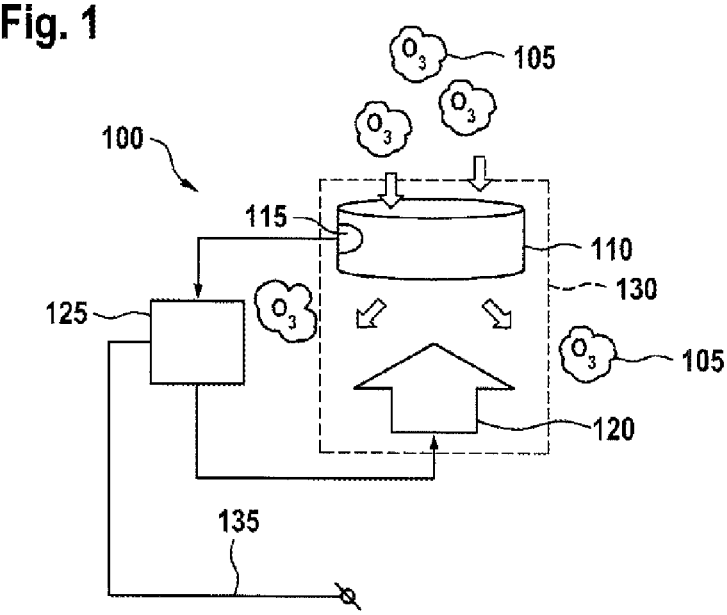
FIG. 1 shows a measuring device for determining a gas concentration.

FIG. 1 shows a measuring device 100 for determining a concentration of a gas 105 which, in particular, can be present in surrounding air. The measuring device 100 comprises a gas-sensitive element 110, a sensing device 115 for determining a parameter of the element 110, a stimulation unit 120 and a processing unit 125. In a preferred embodiment, the gas-sensitive element 110, the sensing device 115 and the stimulation unit 120 are combined with one another to form an integrated sensor 130.

The gas-sensitive element 110 has the property of absorbing some of the gas 105 out of the surroundings and, depending on the absorption that has taken place, of changing a parameter, which can be determined by means of the sensing device 115. In one embodiment, the element 110 comprises a metal oxide, the resistance of which changes, the more of the gas 105 is absorbed in the element 110. Whether the parameter rises or falls with rising concentration of the gas usually depends on the gas and in particular on its oxidation properties. If the element 110 is exposed to a predetermined gas concentration of the gas 105, then it usually takes a time interval in the minute range until so much of the gas 105 is absorbed in the element 110 that the parameter no longer changes. This state is called the equilibrium state. The element 110 attempts to assume the equilibrium state by absorbing or desorbing gas 105, depending on the concentration of the gas 105 in the surroundings. If more or less of the gas 105 is absorbed in the element 110 than corresponds to the concentration of the gas 105 in the surroundings, then the element 110 is in the non-equilibrium state.

The desorption of gas 105 out of the element 110, that is to say the expulsion of gas particles out of the element 110, can be promoted by means of the stimulation unit 120. The stimulation unit 120 can, for example, comprise a light source, in particular a light-emitting diode, the light emitted from which has a predetermined wavelength. This wavelength can comprise about 450 nm, for example. In other exemplary embodiments, the stimulation unit 120 can also be set up to heat the element 110 or to produce an electric field in the area of the element 110.

The processing unit 125 is set up to control the stimulation unit 120 on the basis of the parameter of the element 110 that is determined by means of the sensing device 115, in such a way that the element 110 is in a predetermined non-equilibrium with respect to the surrounding gas concentration. Here, the process is to be carried out in particular periodically or intermittently by the stimulation unit 120 being alternately activated and deactivated. How long the individual activation or deactivation phases last can depend in particular on the parameter of the element 110. Furthermore, the processing unit 125 should be set up to determine a rate of change of the parameter of the element 110 and the concentration of the gas 105 in the area of the element 110 on the basis of the rate of change. Preferably, an interface 135 is provided, via which the processing unit 125 can provide a result of the concentration determination of the gas 105 externally.

Figure 2:
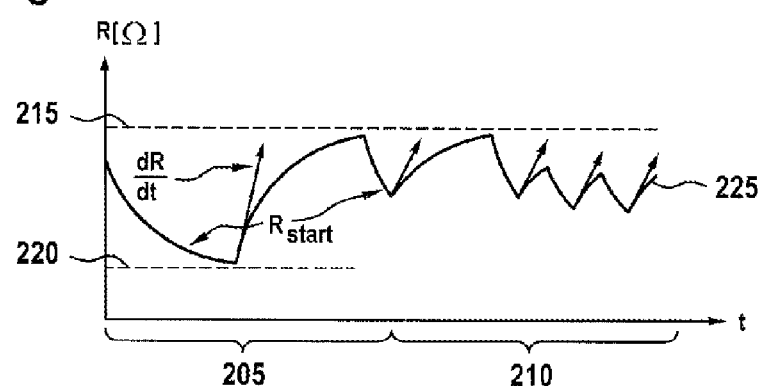
FIG. 2 shows a curve of a parameter dependent on the gas concentration on the measuring device from FIG. 1.

The measuring principle will be described in more detail below with reference to FIG. 2. FIG. 2 shows a curve 225 of a parameter of the element 110 on the measuring device 100 from FIG. 1. In the embodiment illustrated, the parameter of the element 110 is intended to be a resistance, which is plotted in the vertical direction in the graph illustrated and which rises with a rising quantity of absorbed gas 105 in the element 110. In other embodiments, however, another parameter, for example a generated voltage or a current, of the element 110 can be involved, and the relationship between the parameter and the concentration can also be inverted with respect to the illustration of FIG. 2. Plotted in the horizontal direction is a time. Illustrated in a left-hand area is an equilibrium measurement 205 (equilibrium: GG)

and, in a right-hand area, a non-equilibrium measurement 210 (non-equilibrium: NGG).

Also illustrated are a first equilibrium 215 without the influence of the stimulation unit 120 and a second equilibrium 220 under the influence of the stimulation unit 120. If the stimulation unit 120 is active, then the curve 225 initially falls more quickly and then more and more slowly and adheres to the second equilibrium 220. In a corresponding way, when the stimulation unit 120 is switched off, the curve 225 initially rises quickly and then more and more slowly and adheres to the first equilibrium 215.

Within the context of the equilibrium measurement 205, in a first phase the gas 105 absorbed in the element 110 can be desorbed under the influence of the stimulation unit 120, so that, after the stimulation unit 120 has been switched off, the first equilibrium 215 is reached by the curve 225 after a predetermined time and the parameter can be determined. The equilibrium measurement 205 is relatively time-consuming and energy-intensive.

It is therefore proposed, within the context of a non-equilibrium measurement 210, by means of alternating activation and deactivation of the stimulation unit 120, deliberately to bring about a non-equilibrium state, which lies between the equilibria 215 and 220. Preferably, the parameter of the curve 225 is kept in a predetermined range between the equilibria 215 and 220, for example by maintaining a predetermined range from relative equilibria, for example between 20% and 80%. The form of the curve sections of the curve 225 with and without activated stimulation unit 120 is known and usually follows an inverse e-function. To determine the concentration of gas 105 on the element 110, it may therefore be sufficient to determine a characteristic influencing factor of the curve segment. This influencing factor can in particular comprise the slope of the curve 225 at a predetermined time or in a predetermined time period, in particular at the start of a curve section. In each case immediately after the stimulation unit 120 has been switched off, these slopes are plotted as rates of change in the illustration of FIG. 2.

On the basis of a rate of change, the associated gas concentration can be determined by means of the following formula in accordance with the power law:

$$K = A \cdot \left(\frac{dR}{dt}\right)^B \qquad \text{(equation 1)}$$

with:
K=gas concentration
A, B=constants
R=parameter.

Usually, the constant B is about 2 so that, by means of correctly choosing the constant A, the mapping of the rate of change of the determined parameter of the curve 225 onto the gas concentration K can be carried out. In particular, it may be sufficient for any desired, known gas concentration K to determine the constant A by using the determined rate of change of the parameter in order to calibrate the measuring device 100. If the measuring device 100 is arranged in a mobile device, for example, then the concentration of ozone can be interrogated by means of a trustworthy web service in order to carry out this adjustment.

Figure 3:
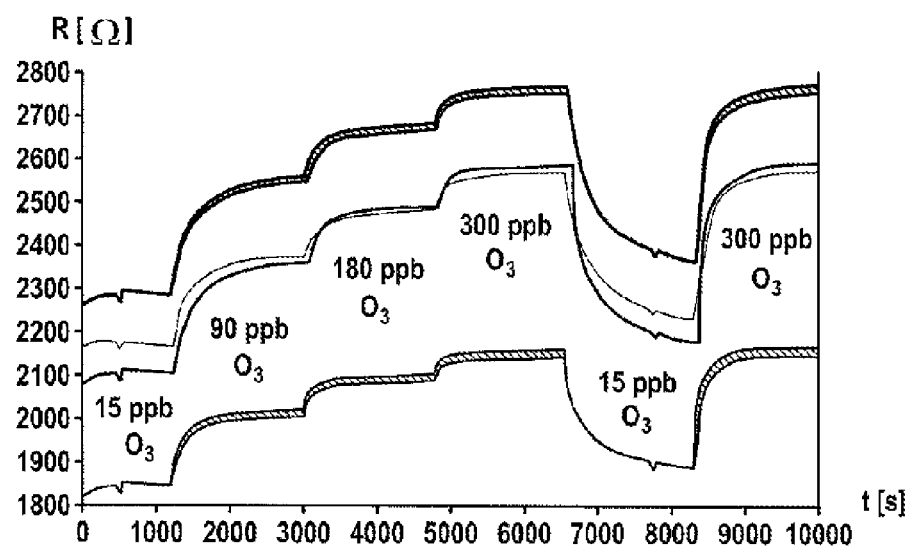
FIG. 3 shows curves of a measured signal with different gas concentrations according to different measuring principles.
Figure 3:
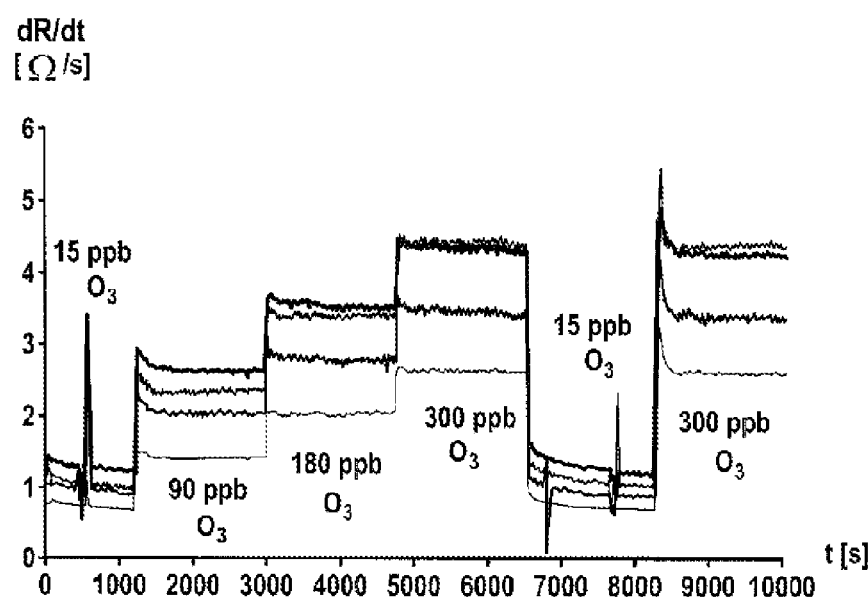

FIG. 3 shows exemplary curves of a measured signal with different gas concentrations in accordance with different measuring principles. In an upper illustration, the determination is carried out by means of equilibrium measurement 205 and, in the lower area, by means of non-equilibrium measurement 210, as explained in more detail above with reference to FIG. 2. The numerical values specified, in particular for gas concentrations, resistances and times, are exemplary. The gas to be determined is ozone here, although this is likewise only an example which can represent many different gases.

For the measured signals illustrated, the gas-sensitive element 110 was exposed to different concentrations of ozone, which are plotted in the illustrations, at intervals of 30 minutes. In each graph, it is possible to see four measured curves, which are assigned to four identical gas-sensitive elements 110. The differences between the measuring curves indicate the scatter between the gas-sensitive elements 110.

It can be seen that, after the equilibrium measurement 205, in each case several minutes are required in order to determine the correct concentration, whereas a considerably faster determination is possible by means of the non-equilibrium measurement 210. It can also be seen that the curves of the four gas-sensitive elements can be brought into coincidence with one another by means of a simple adjustment.

Figure 4:
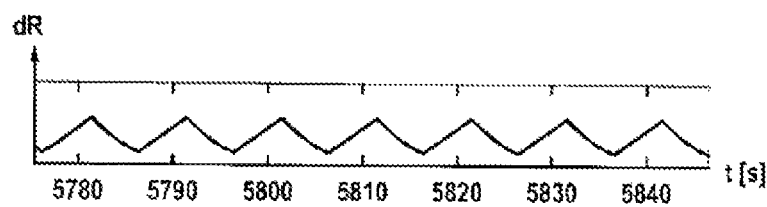
FIG. 4 shows the curve of the parameter on the gas-sensitive element during the measurement according to FIG. 3.

FIG. 4 shows the variation of the parameter of the curve 225 from FIG. 2 that can be determined on the gas-sensitive element 110 over time during the determination according to FIG. 3. The stimulation unit 120 was switched on and off in a five-second cycle. In other embodiments, a mark-space ratio differing from 1:1 or a period length other than 10 seconds can also be used.

Figure 5:
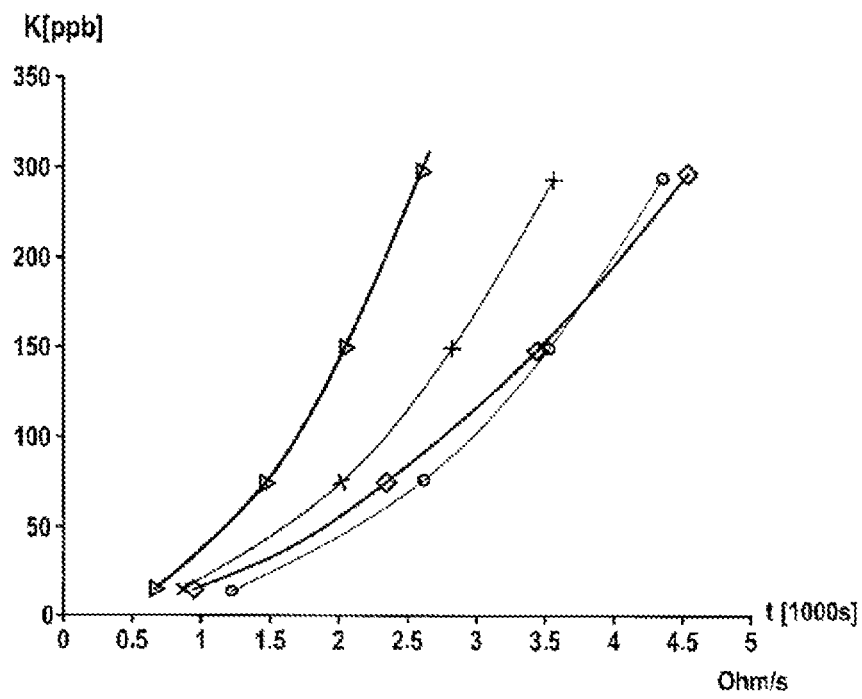
FIG. 5 shows gas concentrations which were determined on the basis of the relationship from FIG. 5.

FIG. 5 shows a mathematical relationship between the rate of change of the parameter on the measuring device 100 from FIG. 1 and a gas concentration K. The numerical values illustrated are once more exemplary and four different measuring curves are assigned to four identical gas-sensitive elements 110. The curves illustrated were created with reference to specific rates of change, which were each determined immediately after the stimulation unit 120 had been switched off. It is obvious that the relationship illustrated follows the power law.

Figure 6:
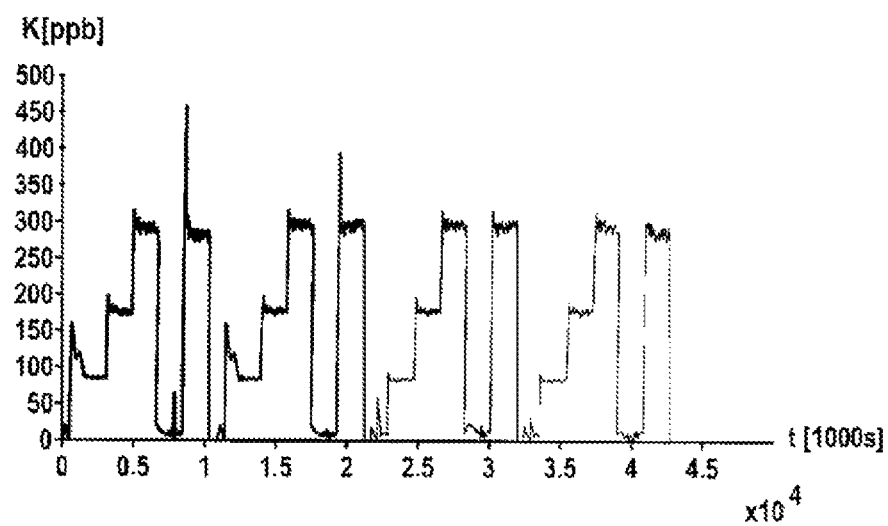
FIG. 6 shows measured values which were determined on the basis of the relationship from FIG. 5.

FIG. 6 shows exemplary gas concentrations which were determined on the basis of the relationship of FIG. 5.

Figure 7:
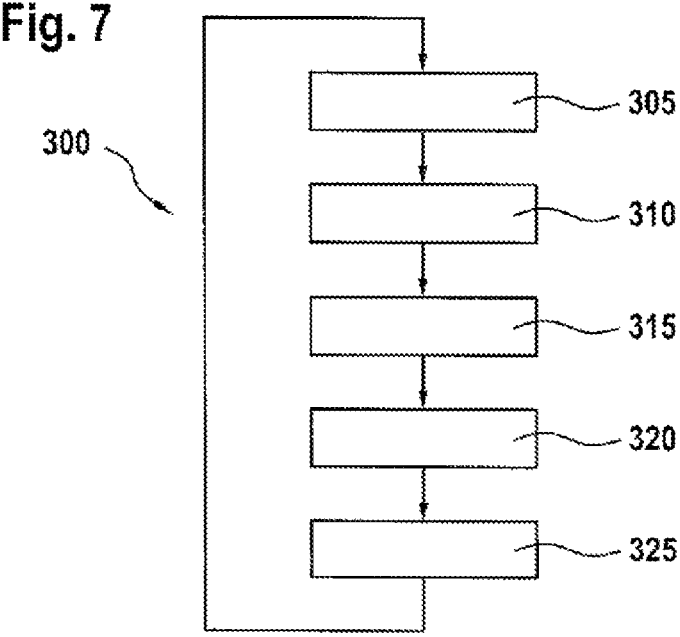
FIG. 7 shows a flowchart of a method for determining a gas concentration.

FIG. 7 shows a flowchart of a method 300 for determining a gas concentration. The method 300 is set up in particular to be performed by means of the measuring device 100 from FIG. 1.

In a step 305, gas 105 is absorbed by the gas-sensitive element 110. This process lasts for a predetermined time, wherein the gas 105 is initially enriched quickly and then more and more slowly on the gas-sensitive element 110 (cf. FIG. 2), until finally an equilibrium state 215 between the absorbed gas 105 and the gas 105 present in the surroundings of the element 110 is reached.

In a step 310, the rate of change of a parameter of the element 110 is determined. The parameter indicates the quantity of gas 105 absorbed on the gas-sensitive element 110 and can be determined in particular on the basis of the crossover behavior of a transistor which comprises the element 110, or the electrical resistance of the element 110.

In an optional step 315, the element 110 is stimulated in order to reduce the quantity of gas 105 accumulated on the element 110. Preferably, the stimulation comprises heating the element 110, for example by means of an external heating element or by an electrical current through the element 110 being brought about. The simulation effects expulsion of accumulated gas 105 out of the element 110, wherein the quantity of bound gas initially falls quickly and then more and more slowly, until a second equilibrium state

220 is reached. The intensity and duration of the stimulation is preferably managed in such a way that the concentration of the gas 105 in the element 110 lies between the two equilibrium states 215 and 220.

In a step 320, the gas concentration in the area of the element 110 on the basis of the rate of change In a step 320, the gas concentration in the area of the element 110 is determined on the basis of the rate of change of the parameter. Here, the determination preferably relates to a predetermined time period which lies as immediately as possible after the end of the stimulation in step 315, when the rate of change is still high. In a further embodiment, the gas concentration can also be determined on the basis of the rate of change of the parameter during the stimulation. It is also possible for both rates of change to be used as a basis for determining the gas concentration.

Then, in a step 325, an optional pause can be inserted in order to permit the enrichment of gas 105 on the element. The method 300 can then return to step 305 and run through again.

What is claimed is:

1. A method of determining a gas concentration, comprising:
    using a gas-sensitive element to absorb a gas;
    determining a rate of change within a predetermined time period of a parameter of the element that depends on a quantity of gas absorbed by the element;
    stimulating the element to accelerate desorption of the gas out from the element, such that a concentration of the gas in the element lies outside of an equilibrium state; and
    determining the gas concentration based on the rate of change.

2. The method of claim 1, wherein the stimulating is performed periodically to keep the concentration of the gas in the element within a predetermined range.

3. The method of claim 2, wherein the gas concentration is determined at least in part based on the rate of change immediately after the stimulating has concluded.

4. The method of claim 1, wherein the gas concentration is determined with reference to a relationship defined by the equation:

$$K = A \cdot \left(\frac{dR}{dt}\right)^B$$

where K is the gas concentration, R is the parameter, B is a constant value equal to about 2, and A is a constant value.

5. The method of claim 1, further comprising determining the parameter electrically.

6. The method of claim 1, wherein the stimulating includes a heating process.

7. The method of claim 1, wherein the stimulating includes an irradiation process using a light having a predetermined wavelength.

8. The method of claim 1, wherein the stimulating includes applying an electric field.

9. A measuring device for determining a gas concentration, comprising:
    a gas-sensitive element configured to absorb a gas;
    a sensing device configured to determine a parameter of the element, the parameter depending on a quantity of the gas absorbed by the gas-sensitive element;
    a stimulation unit configured to stimulate the element in order to accelerate desorption of the gas out from the gas-sensitive element; and
    a processing unit configured to:
        determine a rate of change of the parameter in a predetermined time period;
        control the stimulation unit such that a concentration of the gas in the gas-sensitive element lies outside of an equilibrium state; and
        determine the gas concentration with reference to the rate of change.

10. The measuring device of claim 9, wherein the gas-sensitive element includes a metal oxide.

* * * * *